US009616103B2

(12) United States Patent
Kiselev et al.

(10) Patent No.: US 9,616,103 B2

(45) Date of Patent: Apr. 11, 2017

(54) PHARMACEUTICAL COMPOSITION FOR STIMULATION OF ANGIOGENESIS

(71) Applicant: "NEXTGEN" COMPANY LIMITED, Moscow (RU)

(72) Inventors: Sergej L'vovich Kiselev, Moscow (RU); Roman Vadimovich Deev, St.-Petersburg (RU); Ivan Ivanovich Vorob'ev, Moscow (RU); Nadezhda Aleksandrovna Orlova, Moscow (RU); Artur Aleksandrovich Isaev, Moscow (RU)

(73) Assignee: "NEXTGEN" COMPANY LIMITED, Moscow (RU)

( * ) Notice: Subject to any disclaimer, the term of this patent is extended or adjusted under 35 U.S.C. 154(b) by 0 days.

(21) Appl. No.: 14/423,532

(22) PCT Filed: Aug. 2, 2013

(86) PCT No.: PCT/RU2013/000669

§ 371 (c)(1),
(2) Date: Feb. 24, 2015

(87) PCT Pub. No.: WO2014/035289

PCT Pub. Date: Mar. 6, 2014

(65) Prior Publication Data

US 2015/0335711 A1 Nov. 26, 2015

(30) Foreign Application Priority Data

Aug. 31, 2012 (RU) ................................ 2012137126

(51) Int. Cl.

| | |
|---|---|
| ***A61K 48/00*** | (2006.01) |
| ***A61K 38/18*** | (2006.01) |
| ***A61K 31/7088*** | (2006.01) |
| ***C12N 15/12*** | (2006.01) |
| ***A61K 47/26*** | (2006.01) |
| ***C07K 14/515*** | (2006.01) |

(52) U.S. Cl.

CPC .......... *A61K 38/18* (2013.01); *A61K 38/1866* (2013.01); *A61K 47/26* (2013.01); *C07K 14/515* (2013.01); *A61K 48/00* (2013.01)

(58) Field of Classification Search

None

See application file for complete search history.

(56) References Cited

U.S. PATENT DOCUMENTS

| | | | | |
|---|---|---|---|---|
| 6,613,563 | B1 * | 9/2003 | Sosnowski | C07K 14/50 424/130.1 |
| 6,627,436 | B2 | 9/2003 | Sorge et al. | |
| 2003/0203844 | A1 * | 10/2003 | Delfani | A61K 38/1858 514/8.1 |
| 2008/0081366 | A1 | 4/2008 | Musunuri et al. | |
| 2011/0117107 | A1 * | 5/2011 | Stiles | A61K 31/7088 424/158.1 |
| 2011/0178158 | A1 | 7/2011 | Benet Ferrus et al. | |

FOREIGN PATENT DOCUMENTS

| | | |
|---|---|---|
| CN | 1351055 | 5/2002 |
| CN | 1389269 | 1/2003 |
| RU | 2 297 848 | 4/2007 |
| RU | 2 376 373 | 12/2009 |
| WO | WO 00/47235 | 8/2000 |
| WO | WO 2004/050126 | 6/2004 |
| WO | 2006 029908 | 3/2006 |
| WO | 2006 074182 | 7/2006 |

OTHER PUBLICATIONS

Written Opinion of the International Searching Authority Issued Jan. 23, 2014 in PCT/RU13/000669 Filed Aug. 2, 2013.

International Search Report Issued Jan. 23, 2014 in PCT/RU13/000669 Filed Aug. 2, 2013.

Office Action issued Jan. 7, 2016, in Canadian Patent Application No. 2,881,799.

Anghel et al, "Clinical improvement after treatment with VEGF165 in patients with severe chronic lower limb ischaemia", 2007, Genomic Med., vol. 1, No. 1-2, pp. 47-55.

Schender, V.O., et al., "Simulating the *E.coli* Producer pCMV-VEGF165 Recombinant Strain Fermentation for Therapeutic Plasmid DNA Production", The Russian Chemical and Technology University Named After Mendeleev D.I., pp. 30-31, (May 24, 2011) (with English translation).

"Neovasculgen", Registration Certificate for Pharmaceutical Composition for Medical Application, LP0-00671, URL:http://hsci.ru/o-kompanii/litsenzii, Total 1 Page, (Sep. 28, 2011).

"Instruction for medical application of Neovasculgen®", URL:http://medi.ru/doc/a4101.htm, pp. 1-4, (Mar. 2012).

(Continued)

*Primary Examiner* — Maria Marvich

(74) *Attorney, Agent, or Firm* — Oblon, McClelland, Maier & Neustadt, L.L.P.

(57) ABSTRACT

Provided is a pharmaceutical composition for growth induction in blood vessel tissue which contains purified plasmid DNA encoding a vascular endothelial growth factor (VEGF) and pharmaceutically acceptable excipients that include a cryoprotectant as a vehicle and/or a pH stabilizer for stabilizing the pH in the range of 7.0 to 9.0, in effective quantities. Also provided is a storage method of plasmid DNA which encodes a VEGF comprising mixing the purified plasmid DNA with a solution of at least one cryoprotectant having properties of a vehicle and/or a pH stabilizer in the pH range of 7.0-9.0. The solution is lyophilized and stored at +2 to +8° C. Supercoiled DNA pCMV-VEGF165 may be used which is produced by culturing *Esherichia coli* strain TOP10/pCMV-VEGF165. The pharmaceutical composition is administered to a human in quantities sufficient to provide a necessary therapeutic effect. The provided pharmaceutical composition of plasmid DNA pCMV-VEGF165 does not change significantly properties of the active substance when stored for a long time at a temperature from +2 to +8° C.

19 Claims, 2 Drawing Sheets

(56) References Cited

OTHER PUBLICATIONS

"Neovasculgen®", URL: http://medi.ru/doc/a410100.htm, pp. 1-2, (Apr. 2012) Printed on Jul. 10, 2013.

"Safety and Efficacy Study Using Gene Therapy for Critical Lumb Ischemia", clinicaltrials.gov, pp. 1-4, (Mar. 5, 2012).

"Efficacy and Safety Study of NV1FGF in Patients With Severe Peripheral Artery Occlusive Disease. (TALISMAN202)", clinicaltrials.gov, pp. 1-3, (Nov. 24, 2008).

Shvalb, P.G., et al., "Efficacy and safety of application «Neovasculgen» in the complex treatment patients with chronic lower limb ischemia(IIb-III phase of clinical trials)", Clinical Experiment, vol. I, No. 3, Total 8 Pages, (2011) (with English abstract).

Kusumanto, Y.H., et al., "Treatment with intramuscular vascular endothelial growth factor gene compared with placebo for patients with diabetes mellitus and critical limb ischemia: a double-blind randomized trial.", Hum Gene Ther., URL: http://www.ncbi.nlm.nih.gov/pubmed/16776576, vol. 17, No. 6, Total 1 Page, (Jun. 2006) (English translation only).

Certificate of Conformity Russian Federal Agency for Technical Regulation and Metrology, valid from Sep. 14, 2012 to Jun. 1, 2014 No. 0901087—w/English translation.

"Neovasculgen®", Marketing Authorization for Medical Application of a Pharmaceutical Substance, LP0-00671, URL:http://hsci.ru/o-kompanii/litsenzii, Total 1 Page, (Sep. 28, 2011) w/English translation.

* cited by examiner

SEQUENCE LISTING

```
<160> NUMBER OF SEQ ID NOS: 2

<210> SEQ ID NO 1
<211> LENGTH: 4859
<212> TYPE: DNA
<213> ORGANISM: Artificial Sequence
<220> FEATURE:
<223> OTHER INFORMATION: expression plasmid
<220> FEATURE:
<221> NAME/KEY: exon
<222> LOCATION: (392)..(964)

<400> SEQUENCE: 1

tatgccaagt acgcccccta ttgacgtcaa tgacggtaaa tggcccgcct ggcattatgc     60

ccagtacatg accttatggg actttcctac ttggcagtac atctacgtat tagtcatcgc    120

tattaccatg gtgatgcggt tttggcagta catcaatggg cgtggatagc ggtttgactc    180

acggggattt ccaagtctcc accccattga cgtcaatggg agtttgtttt ggcaccaaaa    240

tcaacgggac tttccaaaat gtcgtaacaa ctccgcccca ttgacgcaaa tgggcggtag    300
```

```
gcgtgtacgg tgggaggtct atataagcag agctggttta gtgaaccgtc agatccgcta    360

gtggatccaa agaattcggg cctccgaaac c atg aac ttt ctg ctg tct tgg       412
                                   Met Asn Phe Leu Leu Ser Trp
                                   1               5

gtg cat tgg agc ctt gcc ttg ctg ctc tac ctc cac cat gcc aag tgg      460
Val His Trp Ser Leu Ala Leu Leu Leu Tyr Leu His His Ala Lys Trp
        10                  15                  20

tcc cag gct gca ccc atg gca gaa gga gga ggg cag aat cat cac gaa      508
Ser Gln Ala Ala Pro Met Ala Glu Gly Gly Gly Gln Asn His His Glu
    25                  30                  35

gtg gtg aag ttc atg gat gtc tat cag cgc agc tac tgc cat cca atc      556
Val Val Lys Phe Met Asp Val Tyr Gln Arg Ser Tyr Cys His Pro Ile
40                  45                  50                  55

gag acc ctg gtg gac atc ttc cag gag tac cct gat gag atc gag tac      604
Glu Thr Leu Val Asp Ile Phe Gln Glu Tyr Pro Asp Glu Ile Glu Tyr
                60                  65                  70

atc ttc aag cca tcc tgt gtg ccc ctg atg cga tgc ggg ggc tgc tgc      652
Ile Phe Lys Pro Ser Cys Val Pro Leu Met Arg Cys Gly Gly Cys Cys
            75                  80                  85

aat gac gag ggc ctg gag tgt gtg ccc act gag gag tcc aac atc acc      700
Asn Asp Glu Gly Leu Glu Cys Val Pro Thr Glu Glu Ser Asn Ile Thr
        90                  95                  100

atg cag att atg cgg atc aaa cct cac caa ggc cag cac ata gga gag      748
Met Gln Ile Met Arg Ile Lys Pro His Gln Gly Gln His Ile Gly Glu
    105                 110                 115

atg agc ttc cta cag cac aac aaa tgt gaa tgc aga cca aag aaa gat      796
Met Ser Phe Leu Gln His Asn Lys Cys Glu Cys Arg Pro Lys Lys Asp
120                 125                 130                 135

aga gca aga caa gaa aat ccc tgt ggg cct tgc tca gag cgg aga aag      844
Arg Ala Arg Gln Glu Asn Pro Cys Gly Pro Cys Ser Glu Arg Arg Lys
                140                 145                 150

cat ttg ttt gta caa gat ccg cag acg tgt aaa tgt tcc tgc aaa aac      892
His Leu Phe Val Gln Asp Pro Gln Thr Cys Lys Cys Ser Cys Lys Asn
            155                 160                 165

aca gac tcg cgt tgc aag gcg agg cag ctt gag tta aac gaa cgt act      940
Thr Asp Ser Arg Cys Lys Ala Arg Gln Leu Glu Leu Asn Glu Arg Thr
        170                 175                 180

tgc aga tgt gac aag ccg agg cgg tgacccgggt ggggtaccag gtaagtgtac     994
Cys Arg Cys Asp Lys Pro Arg Arg
    185                 190

ccaattcgcc ctatagtgag tcgtattaca attcactggc cgtcgtttta caacgtcgtg   1054

actgggaaaa ccctggcgtt acccaactt aatcgccttg cagcacatcc ccctttcgc    1114

cagctggcgt aatagcgaag aggcccgcaa cgaatcgccc cttcccaaca gttgcgcaag   1174

cctgaatggc cgaatggaga tccaattttt aagtgtataa tgtgttaaac tactgattct   1234

aattgtttgt gtattttaga ttcacagtcc caaggctcat ttcaggcccc tcagtcctca   1294

cagtctgttc atgatcataa tcagccatac cacatttgta gaggttttac ttgctttaaa   1354

aaacctccca cacctccccc tgaacctgaa acataaaatg aatgcaattg ttgttgttaa   1414

cttgtttatt gcagcttata atggttacaa ataaagcaat agcatcacaa atttcacaaa   1474

taaagcattt ttttcactgc attctagttg tggtttgtcc aaactcatca atgtatctta   1534

aggcgtaaat tgtaagcgtt aatattttgt taaaattcgc gttaaatttt tgttaaatca   1594

gctcattttt taaccaatag gccgaaatcg gcaaaatccc ttataaatca aaagaataga   1654

ccgagatagg gttgagtgtt gttccagttt ggaacaagag tccactatta aagaacgtgg   1714
```

```
actccaacgt caaagggcga aaaaccgtct atcagggcga tggcccacta cgtgaaccat   1774
caccctaatc aagttttttg gggtcgaggt gccgtaaagc actaaatcgg aaccctaaag   1834
ggagcccccg atttagagct tgacggggaa agccggcgaa cgtggcgaga aaggaaggga   1894
agaaagcgaa aggagcgggc gctagggcgc tggcaagtgt agcggtcacg ctgcgcgtaa   1954
ccaccacacc cgccgcgctt aatgcgccgc tacagggcgc gtcaggtggc acttttcggg   2014
gaaatgtgcg cggaacccct atttgtttat ttttctaaat acattcaaat atgtatccgc   2074
tcatgagaca ataaccctga taaatgcttc aataatattg aaaaaggaag agtcctgagg   2134
cggaaagaac cagctgtgga atgtgtgtca gttagggtgt ggaaagtccc caggctcccc   2194
agcaggcaga agtatgcaaa gcatgcatct caattagtca gcaaccaggt gtggaaagtc   2254
cccaggctcc ccagcaggca gaagtatgca aagcatgcat ctcaattagt cagcaaccat   2314
agtcccgccc ctaactccgc ccatcccgcc cctaactccg cccagttccg cccattctcc   2374
gccccatggc tgactaattt tttttattta tgcagaggcc gaggccgcct cggcctctga   2434
gctattccag aagtagtgag gaggcttttt tggaggccta ggcttttgca aagatcgatc   2494
aagagacagg atgaggatcg tttcgcatga ttgaacaaga tggattgcac gcaggttctc   2554
cggccgcttg ggtggagagg ctattcggct atgactgggc acaacagaca atcggctgct   2614
ctgatgccgc cgtgttccgg ctgtcagcgc aggggcgccc ggttcttttt gtcaagaccg   2674
acctgtccgg tgccctgaat gaactgcaag acgaggcagc gcggctatcg tggctggcca   2734
cgacgggcgt tccttgcgca gctgtgctcg acgttgtcac tgaagcggga agggactggc   2794
tgctattggg cgaagtgccg gggcaggatc tcctgtcatc tcaccttgct cctgccgaga   2854
aagtatccat catggctgat gcaatgcggc ggctgcatac gcttgatccg gctacctgcc   2914
cattcgacca ccaagcgaaa catcgcatcg agcgagcacg tactcggatg gaagccggtc   2974
ttgtcgatca ggatgatctg gacgaagagc atcaggggct cgcgccagcc gaactgttcg   3034
ccaggctcaa ggcgagcatg cccgacggcg aggatctcgt cgtgacccat ggcgatgcct   3094
gcttgccgaa tatcatggtg gaaaatggcc gcttttctgg attcatcgac tgtggccggc   3154
tgggtgtggc ggaccgctat caggacatag cgttggctac ccgtgatatt gctgaagagc   3214
ttggcggcga atgggctgac cgcttcctcg tgctttacgg tatcgccgct cccgattcgc   3274
agcgcatcgc cttctatcgc cttcttgacg agttcttctg agcgggactc tggggttcga   3334
aatgaccgac caagcgacgc ccaacctgcc atcacgagat ttcgattcca ccgccgcctt   3394
ctatgaaagg ttgggcttcg gaatcgtttt ccgggacgcc ggctggatga tcctccagcg   3454
cggggatctc atgctggagt tcttcgccca ccctaggggg aggctaactg aaacacggaa   3514
ggagacaata ccggaaggaa cccgcgctat gacggcaata aaaagacaga ataaaacgca   3574
cggtgttggg tcgtttgttc ataaacgcgg ggttcggtcc cagggctggc actctgtcga   3634
taccccaccg agaccccatt ggggccaata cgcccgcgtt tcttcctttt ccccacccca   3694
ccccccaagt tcgggtgaag gcccagggct cgcagccaac gtcggggcgg caggccctgc   3754
catagcctca ggttactcat atatacttta gattgattta aaacttcatt tttaatttaa   3814
aaggatctag gtgaagatcc tttttgataa tctcatgacc aaaatccctt aacgtgagtt   3874
ttcgttccac tgagcgtcag accccgtaga aaagatcaaa ggatcttctt gagatccttt   3934
ttttctgcgc gtaatctgct gcttgcaaac aaaaaaacca ccgctaccag cggtggtttg   3994
tttgccggat caagagctac caactctttt tccgaaggta actggcttca gcagagcgca   4054
gataccaaat actgttcttc tagtgtagcc gtagttaggc caccacttca agaactctgt   4114
```

```
agcaccgcct acatacctcg ctctgctaat cctgttacca gtggctgctg ccagtggcga   4174

taagtcgtgt cttaccgggt tggactcaag acgatagtta ccggataagg cgcagcggtc   4234

gggctgaacg gggggttcgt gcacacagcc cagcttggag cgaacgacct acaccgaact   4294

gagataccta cagcgtgagc tatgagaaag cgccacgctt cccgaaggga gaaaggcgga   4354

caggtatccg gtaagcggca gggtcggaac aggagagcgc acgagggagc ttccaggggg   4414

aaacgcctgg tatctttata gtcctgtcgg gtttcgccac ctctgacttg agcgtcgatt   4474

tttgtgatgc tcgtcagggg ggcggagcct atggaaaaac gccagcaacg cggccttttt   4534

acggttcctg gccttttgct ggccttttgc tcacatgttc tttcctgcgt tatcccctga   4594

ttctgtggat aaccgtatta ccgccatgca ttagttatta atagtaatca attacggggt   4654

cattagttca tagcccatat atggagttcc gcgttacata acttacggta aatggcccgc   4714

ctggctgacc gcccaacgac ccccgcccat tgacgtcaat aatgacgtat gttcccatag   4774

taacgccaat agggactttc cattgacgtc aatgggtgga gtatttacgg taaactgccc   4834

acttggcagt acatcaagtg tatca                                         4859
```

<210> SEQ ID NO 2
<211> LENGTH: 191
<212> TYPE: PRT
<213> ORGANISM: Homo sapiens

<400> SEQUENCE: 2

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

PHARMACEUTICAL COMPOSITION FOR STIMULATION OF ANGIOGENESIS

BACKGROUND OF THE INVENTION

Field of the Invention

An object of the invention pertains to biotechnology, namely a strain producer of plasmid DNA, a relevant pharmaceutical composition which is able to induce growth of blood vessels (vascularization) in the injection site and its application in complex therapy for atherosclerotic lower limb ischemia, as well in treatment of wounds and ulcers of various genesis, and a method for storage of purified plasmid DNA.

Discussion of the Background

Gene therapy with naked plasmid DNA for treatment of diseases or vaccination against pathogens or antigens of tumor cells enables development of finished dosage forms of therapeutic DNA which may be stored, shipped, and used by specialists under unfavorable conditions, and in particular at positive or increased temperatures. Physical and chemical stability of the stored plasmid DNA is significantly defined by a composition of excipients, its concentration and/or the content in the finished dosage form and/or storage conditions (Schleef M., Schmidt T., Animal-free production of ccc-supercoiled plasmids for research and clinical applications, J. Gene Med., 6 Suppl 1:S45-53 (2004)). The main process which affects a pharmaceutically active form of the stored plasmid DNA is degradation of a DNA chain which leads to the formation of relaxed circular plasmid DNA and, subsequently, of a linear two-chain form. It is known that when a frozen plasmid DNA solution is stored at a temperature below minus 80° C., degradation of the supercoiled DNA form is practically unnoticeable (Walther W., Stein U., Voss C., Schmidt T., Schleef M., Schlag P. M., Stability analysis for long-term storage of naked DNA: impact on nonviral in vivo gene transfer, Anal Biochem., 318(2):230-5 (2003)). A such method of storage of plasmid DNA cannot be widely used in clinical practice, as in most cases, healthcare institutions and pharmacies do not have necessary refrigeration equipment. It is rather difficult to ship finished dosage forms and maintain such a low temperature of the product. The selection of appropriate compositions and concentrations of excipients may result in a plasmid DNA solution which is stable for 12 months if stored at 4° C. or over three years if stored at 20° C. (Przybylowski M., Bartido S., Borquez-Ojeda O., Sadelain M., Riviere I., Production of clinical-grade plasmid DNA for human Phase I clinical trials and large animal clinical studies, Vaccine, 25(27):5013-24 (2007)).

The most prevalent method for development of more stable dosage forms is lyophilization. As a rule, lyophilized dosage forms are stable at 4° C. for several years, and in some cases, a product may be stored at room temperature for several months or even two years. Lyophilization also allows to change a concentration of an active substance, wherein vials may be filled with a small amount of a concentrated solution, and the volume may be increased up to the necessary level for product dissolution. Lyophilization of hypotonic solutions and subsequent dissolution of the lyophilizate with a saline solution or a solution with normal osmolality may be used (Anchordoquy T. J., Armstrong T. K., Molina M. C., Low molecular weight dextrans stabilize nonviral vectors during lyophilization at low osmolalities: concentrating suspensions by rehydration to reduced volumes, J Pharm Sci., 94(6):1226-36 (2005)).

Usually, lyophilization of plasmid DNA solutions increases product stability for further storage, but freezing and vacuum sublimation procedures may significantly impair the supercoiled structure of plasmid DNA (Anchordoquy T. J., Armstrong T. K., Molina M. C., Allison S. D., Zhang Y., Patel M. M., et al., Physical stabilization of plasmid DNA-based therapeutics during freezing and drying, In: Costantino H R, Pikal M. J., editors. Lyophilisation of biopharmaceuticals, AAPS press; pp. 605-41 (2004)). In particular, DNA lyophilization from a frozen aqueous solution not containing excipients causes elimination of coordinated water molecules, i.e., a hydrated envelope of a DNA molecule that results in the loss of structural integrity of the DNA molecule (Poxon S. W., Hughes J. A., The effect of lyophilization on plasmid DNA activity, Pharm Dev Technol., 5(1):115-22 (2005)). Consequences of the impaired conformation of a DNA molecule which include degradation of complementary bonds between nitrogen bases and partial degradation of stacking result in undesirable events, i.e., decrease of a biological activity of plasmid DNA up to 25% from the original activity (Anchordoquy T. J., Armstrong T. K., Molina M. C., Low molecular weight dextrans stabilize nonviral vectors during lyophilization at low osmolalities: concentrating suspensions by rehydration to reduced volumes, J Pharm Sci., 94(6):1226-36 (2005)). It is known that a loss of coordinated water molecules eliminated by sublimation may be compensated by the addition of non-volatile hydrophilic substances such as sugars and polyoles to the lyophilized solution (Maitani Y., Aso Y., Yamada A., Yoshioka S., Effect of sugars on storage stability of lyophilized liposome/DNA complexes with high transfection efficiency, Int J Pharm., 356(1-2):69-75 (2008)). A large part of known methods in the field of DNA stabilization by lyophilisation uses freeze-dried lyposomes containing DNA (U.S. Pat. No. 7,323,297), and, therefore, the applicability of know solutions for a solution containing naked plasmid DNA is questionable. In the study of Quaak S., Haanen J., Beijnen J., and Nuijen B., Naked Plasmid DNA Formulation: Effect of Different Disaccharides on Stability after Lyophilisation, AAPS PharmSciTech, Vol. 11, No. 1 (March 2010)), the effect of several polysaccharides on lyophilization of plasmid DNA was examined, and it was established that sucrose which is used with DNA in the mass ratio of 20:1 provided the most stable dosage form for storage. The study did not consider the effect of the pH and a saline solution on stability of plasmid DNA, did not study compositions of isotonic DNA solutions at concentrations below 5 mg/ml, and did not study monosaccharides which are potentially usable for obtaining stable lyophilized macromolecule preparations.

SUMMARY OF INVENTION

An object of the invention pertains to a strain producer of plasmid DNA and a physiologically feasible pharmaceutical composition which provides stability of a finished dosage form of the plasmid DNA for a long time and can be used for gene therapy.

A strain producer of plasmid DNA *Esherichia coli* is TOP10/pCMV-VEGF165 strain which comprises plasmid pCMV-VEGF165 and produces supercoiled DNA of the plasmid pCMV-VEGF165 when cultured in a medium, wherein the strain has been deposited with the Russian Collection of Agricultural Microorganisms at the All-Russia Research Institute for Agricultural Microbiology RCAM ARRIAM RAAS under Accession Number 517.

A pharmaceutical composition comprises a preparation of purified plasmid DNA encoding a vascular endothelial growth factor (VEGF) under the control of functional genetic elements which provide gene expression in human cells, and an effective amount of at least one pharmaceutically acceptable excipient for providing an isotonic solution, wherein the at least one pharmaceutically acceptable excipient is at least one cryoprotectant which is a vehicle, a pH stabilizer or a combination thereof, wherein a concentration of the purified plasmid DNA is from 0.1 to 10 mg/ml, and a pH of the composition is form 7.0 to 9.0. The composition could be used for growth induction in blood vessel tissue.

Another object of the invention is a method for storage of purified plasmid DNA which encodes a vascular endothelial growth factor (VEGF) comprising adding a solution of at least one cryoprotectant to the purified plasmid DNA, thereby obtaining an isotonic solution, subsequently lyophilizing the isotonic solution, and storing the lyophilizate at a temperature of from +2° C. to +8° C. wherein a concentration of the purified plasmid DNA prior to the lyophilizing is from 0.1 to 10 mg/ml, and a pH of the isotonic solution is from 7.0 to 9.0.

The pharmaceutical composition can be used for the preparation of a solution for injections intended for intramuscular, intravenous or intraarterial, subcutaneous and intradermal administration. It can be used for the cutaneous administration as a gel for implantation on a resorbable or non-resorbable carrier.

The pharmaceutical composition is intended for the preparation of a solution ex tempore or otherwise for intramuscular or any other endogenous administration to a subject (patient, injured person, animal) to induce development in blood vessel tissue.

One of the therapeutic indications of the pharmaceutical composition is ischemic conditions of various etiology including a coronary heart disease, lower limb chronic obliterative arterial diseases; situations which the need of reparative tissue processes for correction, for example major, persistent wounds (ulcers), including burns, local damages, including bone fractures and defects.

Another object of the invention is a method for application of the pharmaceutical composition comprising applying an effective amount of the pharmaceutical composition for providing a therapeutic effect depending on a nosologic form and medical indication, to a human subject.

BRIEF DESCRIPTION OF DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
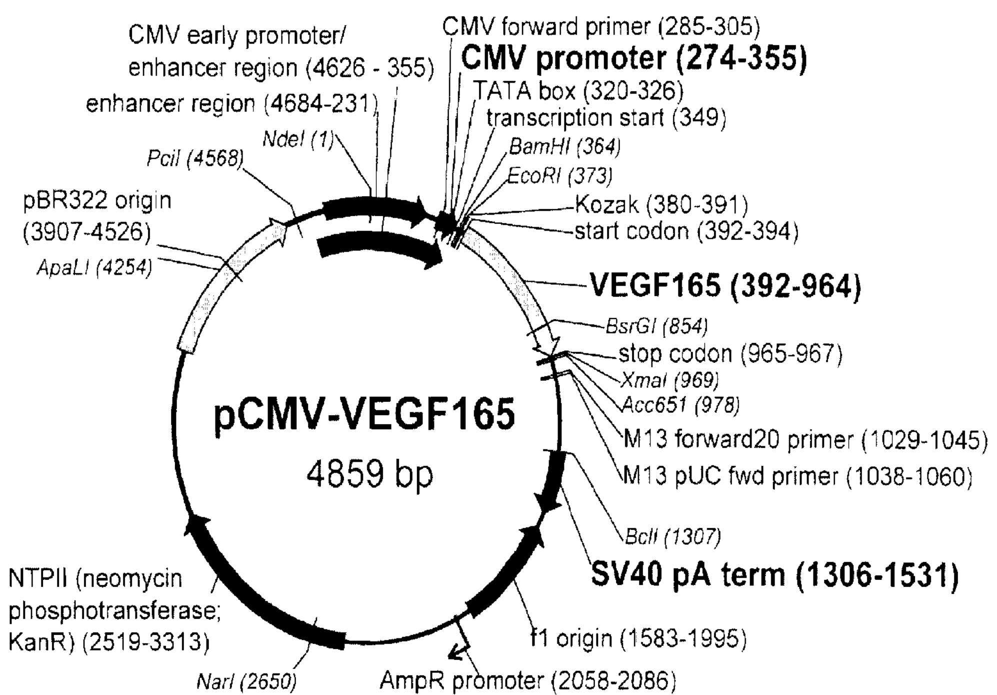
FIG. 1 shows an expression map of plasmid pCMV-VEGF165 (length is 4859 base pairs) (SEQ ID NO: 1). The following abbreviations are used: "CMV early promoter/enhancer region"—a promoter/enhancer region of early genes of cytomegalovirus; an enhancer region; "CMV promoter"—a promoter region of cytomegalovirus; "TATA box"—a TATA-element; "transcription start"—a point of the transcription start; "Kozak"—a Kozak sequence; "start codon"—the first codon of the open reading frame of VEGF165; "VEGF165"—the polypeptide open reading frame (ORF) of the human vascular endothelial growth factor 165; "stop codon"; "SV40 pA term"—a polyadenylation signal and a virus terminator SV40; "CMV forward primer"—the annealing region of the standard primer CMV forward20; "M13 forward20 primer"—the annealing region of the standard primer M13 forward20; "M13 pUC fwd primer"—the annealing region of the standard primer M13 pUC fwd; "pBR322 ori"—the origin region of plasmid replication pBR322; "f1 origin"—the origin region of bacteriophage replication f1; "AmpR promoter"—the prokaryotic promoter of the gene bla; "NTPII (neomycin phosphotransferase; KanR"—the sequence which encodes aminoglycoside-3'-phosphotransferase providing bacterial resistance to kanamycine. The arrows show directions of gene transcription, the numbers of the first and last nucleotide fragments are provided in parentheses. Recognition sites for restriction endonucleases are provided in italics, nucleotides in cutting points are given in parentheses.
Figure 2:
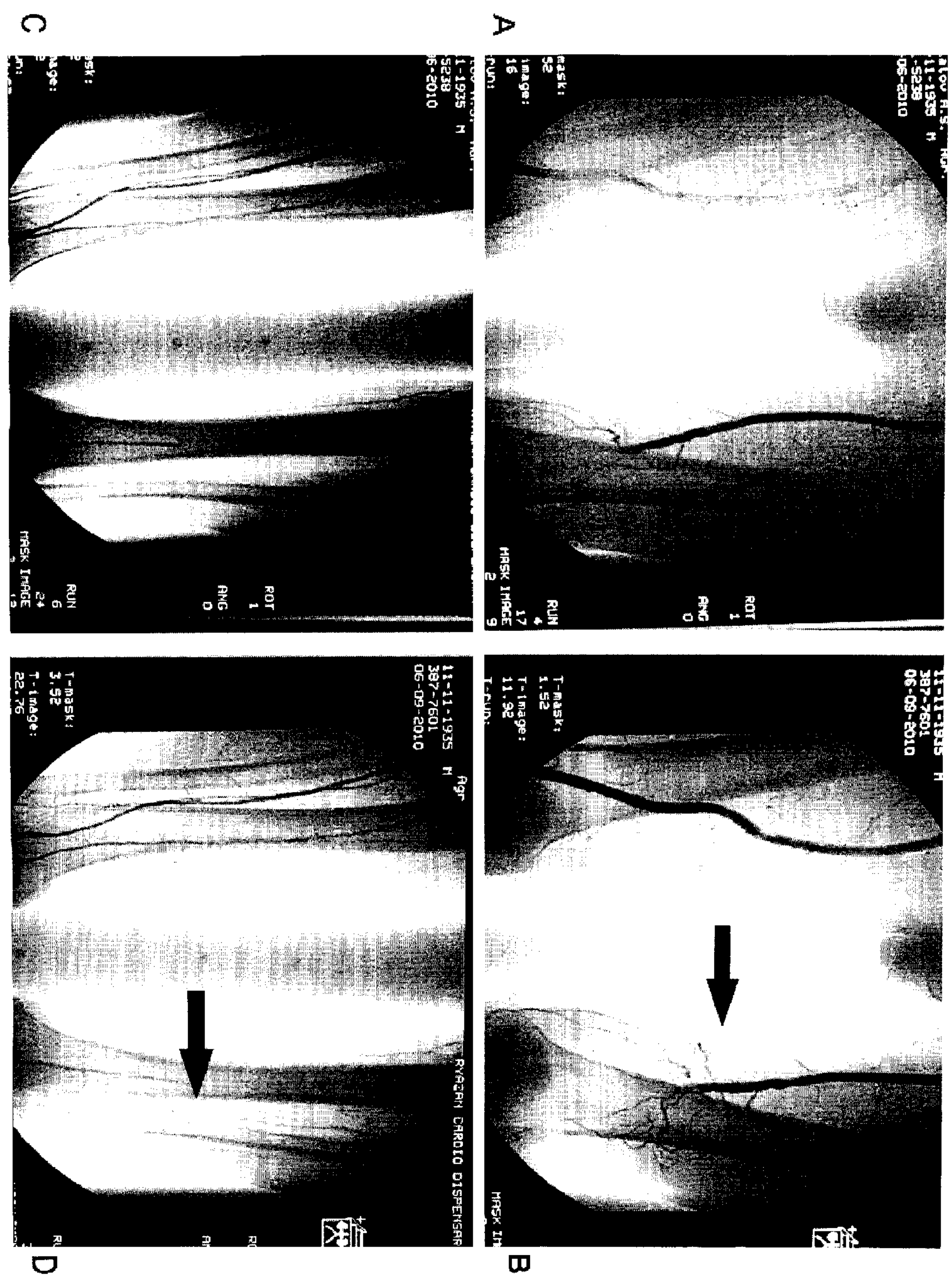
FIG. 2 shown an angiograms of a 74-year patient with chronic lower limb ischemia. Diagnosis: atherosclerosis, bilateral femoropopliteal occlusive disease stage IIb-III (pain at rest). Admission values: ankle-brachial index—0.48 (right), 0.32 (left); transcutaneous partial pressure of oxygen—61 mm Hg. The patient had physical therapy as a part of standard complex treatment (dextranes, disaggregants). Values at 90 days: walking distance—130 m.; ankle-brachial index—0.5 (right), 0.57 (left); transcutaneous partial pressure of oxygen—78 mm Hg. A, B—angiograms prior to treatment: upper and middle one-third of the thigh (A); shank (B); C, D—angiograms at 90 days after the administration of Neovasculgen as a part of complex therapy: upper and middle one-third of the thigh (C); shank (D). Satisfactorily filled blood vessels are shown with arrows including evolving collateral vessels.

All publications, patent applications, patents, and other references mentioned herein are incorporated by reference herein in their entirety. Further, the materials, methods, and examples are illustrative only and are not intended to be limiting, unless otherwise specified. Plasmid DNA which encodes a vascular endothelial growth factor may be obtained by ligation of the open reading frame (ORF) of the human cDNA VEGR with a plasmid vector which provides expression of encoded genes in human cells, as well as plasmid replication in *Esherichia coli* cells. Examples of the vectors may be plasmids pcDNA, pCMV-Script and pBK-CMV (a source-electronic database at Hypertext Transfer Protocol://addgene.org/vector-database/). A necessary component of the vector is an eukaryotic promoter. Non-limiting examples of the promoters include, but not limited to, the cytomegalovirus early promoter/enhancer (CMV), human translation elongation factor 1 alpha (EF1a) promoter, human ubiquitin C (Ubc) promoter, Simian vacuolating virus (SV40) promoter, murine phosphoglycerate kinase 1 (PGK) promoter, and human beta-actin promoter. A more preferable group of vectors for expression of the VEGF are vectors suitable for human cells which contain the immediate early promoter of cytomegalovirus (hereinafter—the CMV promoter), a gene of antibiotic resistance, and a region for a replication origin which provides the moderate or high plasmid copy number which may be, for example, the origin of replication of ColE1, pUC, pBR322, or p15A. A more preferable group of vectors includes a gene providing resistance to antibiotic kanamycine encoding neomycin phosphotransferase (NPT II) which allows to exclude the use of antibiotics of the ampicillin group from the process of making a plasmid. As the vectors for obtaining target plasmid DNA, plasmids encoding an ORF of other genes could be used. The target plasmid DNA may be obtained from such plasmid DNAs by elimination of an ORF region of a heterogeneous gene with the use of restriction endonucleases, isolation of the acceptor DNA fragment and its subsequent ligation with the donor DNA fragment which encodes the ORF of the human cDNA VEGF. An example of the acceptor plasmid may be plasmid pEGFP-N2. A region of the open reading frame of the human cDNA VEGF may be selected from, for example, four known splice variants which encode VEGF isoforms having a length of 121, 145, 165, or 189 amino acids. A more preferred VEGF isoform for obtaining plasmid DNA is the splice variant having the length of 165 amino acids. The ORF region of the human cDNA VEGF may be derived from the total cDNA of human tissue or synthesized from the overlaying oligonucleotides.

In the synthetic part of the ORF of the human cDNA VEGF, a part or all codons may be replaced by degenerated codons. The synthetic fragment of cDNA can substitute the natural region if it provides the life time of cDNA and efficiency of the target gene translation comparable to that of the natural fragment. cDNA of the VEGF which is used for obtaining a target plasmid may contain known polymorphism (substitution of isolated nucleotides) which does not change the amino acid composition of the encoded polypeptide. The use of cDNA of the VEGF which contains such polymorphism does not change properties of the derived target plasmid. A more preferable plasmid which encodes VEGF and is intended for the medical use is a ligation product of the ORF of the VEGF region of the isoform having 165 amino acids and the acceptor fragment of plasmid pBK-CMV.

Plasmid DNA pCMV-VEGF165, which is described in patent RU2297848, is 4859 base pairs long and has the nucleotide sequence of SEQ ID NO: 1. The structure of the plasmid pCMV-VEGF165 is presented on FIG. 1.

The plasmid having 4859 base pairs (SEQ ID NO: 1) comprises:

1. The region between nucleotides 1-361, from the sequence between nucleotides 968-4859 of the vector pBK-CMV, which includes:

1.1. the elements which provide expression of a target gene in mammalian cells: the CMV early promoter/enhancer region (nucleotides 4626-355) which include the enhancer region (nucleotides 4684-231) and the cytomegalovirus promoter (nucleotides 274-355); the TATA box-element (nucleotides 320-326); the transcription start (349); the polyadenylation signal and the virus SV40 terminator (nucleotides 1306-1531); and 1.2. the elements which maintain the presence of the plasmid in bacterial cells, the region of the initiation of bacteriophage replication f1 (nucleotides 1583-1995); the prokaryotic promoter of the gene bla (nucleotides 2058-2086); the sequence which encodes aminoglycoside-3'-phosphotransferase providing bacterial resistance to kanamycine (nucleotides 2519-3313); and the region of the plasmid replication of pBR322 (nucleotides 3907-4526);

2. The region between nucleotides 362-967, which includes the Kozak sequence (nucleotides 380-391) which is located around the start-codon of a target gene and provides the initiation of translation of mRNA of the target gene, the open reading frame of the gene encoding VEGF 165 (nucleotides 392-964), and the stop-codon (nucleotides 965-967).

The plasmid contains recognition sites for restriction endonucleases NdeI (1); BamHI (364); EcoRI (373); BsrGI (854); XmaI (969); Acc651 (978); Bell (1307); NarI (2650); ApaLI (4254); and PciI (4568).

The plasmid was obtained by using known methods of gene engineering, commercially available plasmids and cloned regions of human cDNA (Sambrook J, Fritsch E F, Maniatis T. Molecular Cloning. 2nd ed. New York, N.Y.: Cold Spring Harbor Laboratory Press; 1989).

The plasmid elements are enlisted as they are located. Mutual positions of the functional elements are important for the effective plasmid activity.

As a recombinant plasmid, in accordance with an object of the invention, various plasmids may be used which contain the gene encoding VEGF165 under the control of an eukaryotic promoter.

DNA fragments which encode the same regulatory elements may be derived by modifying the nucleotide sequence of a DNA fragment (SEQ ID NO: 1), for example, with the use of site-directed mutagenesis, wherein one or more nucleotides in the certain sites may be deleted, inserted or added. The modified DNA fragments, as mentioned above, may be derived with the use of known processing methods for generation mutations.

To obtain a producer strain, plasmid DNA pCMV-VEGF165 may be inserted (transformed) into a bacterial cell, preferably into bacteria of *Escherichia* sp., susceptible to such transformation by the plasmid. The selection of the transformed cells is not crucial, as the methods and approaches of transformation are known. Although depending on the cell type and culture conditions of the derived transformants, the abundance and total content of the plasmid pCMV-VEGF165 in the bacterial suspension may vary, the target plasmid would be present provided successful transformation of the recipient cell.

Plasmid cell transformation implies plasmid introduction into a cell using known methods. Transformation methods include, for example, a method described in Jac A. Nickoloff, Electroporation Protocols for Microorganisms (Methods in Molecular Biology)//Humana Press; 1st edition (Aug. 15, 1995).

According to one embodiment, "a bacterial cell—producer of the plasmid CMV-VEGF165" includes a bacterial cell which has the ability to maintain, replicate and accumulate the plasmid CMV-VEGF165, when the bacterial cell has been cultured in a culture medium. The term "bacterial cell—producer of the plasmid pCMV-VEGF165" means a cell which is able to accumulate the plasmid pCMV-VEGF165 at no less than 1 mg/l (or 1 $\mu g/10^9$ cells), and more preferably, at no less than 10 mg/l. The plasmid pCMV-VEGF165 is accumulated in a cell, preferably, in the supercoiled circular form.

Preferably, bacteria of the *Escherichia* sp. could be used for transformation with the plasmid pCMV-VEGF165 which encodes the gene VEGFR under the control of the CMV promoter. A type of promoter is not particularly limited and could be a promoter active in the myocytes, fibroblasts and endothelium, for example, SV40 or EF-1.

The term "bacterium *Escherichia*" means that the bacterium includes *Escherichia* species in accordance with the classification known in microbiology. As an example of the microorganism belonging to the *Escherichia* species, *E. coli* bacterium may be mentioned.

*Escherichia* species which could be used for transformation are not limited, wherein non-limiting examples of the bacteria are described in the book by Neidhardt, F. C. et al. (*Escherichia coli* and *Salmonella typhimurium*, American Society for Microbiology, Washington D.C., 1208, Table 1).

Preferred recipient strains for production of the plasmid pCMV-VEGF165 are *E. coli* strains that are derived from the non-pathogenic strain K12 which contains an inactivated gene recA1 of the DNA reparation system, as well as an inactivated gene of endonuclease endA1. Examples of such strains are DH5alpha, DH10B, XL-1Blue, and TOP10.

Examples of a recipient strain for production of the plasmid pCMV-VEGF165 include, but not limited to, *Escherichia coli* TOP10. Strain *Escherichia coli* TOP10 is characterized by the cultural morphological, physiological and biochemical signs and genetic features described below.

Strain *Escherichia coli* TOP10/pCMV-VEGF165 has been deposited with the Russian Collection of Agricultural Microorganisms at the All-Russia Research Institute for Agricultural Microbiology RCAM ARRIAM RAAS (ARRIAM, 3 Podbelsky chausse, St. Petersburg, Pushkin 8, 196608, RU) on Feb. 24, 2009, and has been granted the accession number 517.

Cultural morphological particularities of *Escherichia coli* TOP10 are: gram negative rods that form strands; in an agar medium—forms lucid, semi-transparent, convex, moderate even-edged colonies. The strain is stored in the Luria-Bertrani medium containing 1% glucose and 10% glycerol. The strain is cultured in the Luria-Bertani medium.

Genetic particularities of the strain *Escherichia coli* TOP10 are: genotype of the strain—Δ(araA-leu)7697, [araD139]B/r, Δ(codB-lacI)3, ϕ80dlacZ58(M15), galK0, mcrA0, galU-, recA1, endA1, nupG-, rpsL-(strR), Δ(mcrC-mrr)715.

Transformation of the strain *Escherichia coli* TOP10 with the plasmid pCMV-VEGF165 results in the production of the producer strain TOP10/pCMV-VEGF165 which provides biosynthesis of the plasmid pCMV-VEGF165 in the amount of 5-20 mg/1, when cultured in flasks with shaking for 12-20 hours in the Luria-Bertrani medium with the addition of kanamycin up to 30 μg/ml, wherein not less than 70% of the plasmid pCMV-VEGF165 present in the supercoiled form.

A method for preparation of the highly purified plasmid pCMV-VEGF165 includes culturing the abovementioned bacteria in a culture medium suitable for growth of the transformed prokaryotic cells; selecting cell biomass; resuspending the cells; conducting alkaline lysis of the cells; selectively renaturating the plasmid DNA with an acid solution; separating the precipitated pellet; concentrating by ultrafiltration; separating foreign impurities and RNA by gel filtration in a solution having a highly concentration of salt (e.g., saline); separating residual genomic DNA, endotoxin and related impurities by affinity (thiophilic) chromatography; the final purification by anionexchange chromatography and subsequent concentration; and desalinating the solution of the purified plasmid pCMV-VEGF165 with ultrafiltration/diafiltration.

The derived preparation of the plasmid pCMV-VEGF165, which is suitable for further production of a pharmaceutical composition and a finished dosage form, is characterized by the following properties:

1) Proportion of related impurities (relaxed ring and linear forms of the plasmid)—not more than 5% (hereinafter—the proportion of a concentration of an active substance).
2) Proportion of genomic DNA of *E. coli*—not more 1%.
3) Proportion of RNA—not more 1%.
4) Proportion of the total protein—not more 0.1%.
5) Endotoxin content—not more 50 EU/1 mg of the active substance.

A solution of the plasmid DNA pCMV-VEGF165 suitable for further production of a pharmaceutical composition and a finished dosage form may be prepared with the use of other known methods for DNA isolation and purification, for example, using a method of thermal lysis of bacteria in the presence of a detergent, a method of selective RNA precipitation with calcium chloride, a method for separation of supercoiled and relaxed plasmid forms with the gradient elution and other methods described, e.g., in D. M. F. Prazeres, "Plasmid Biopharmaceuticals: Basics, Applications and Manufacturing", John Wiley & Sons, Inc., (2011) ISBN: 978-0-470-23292-7.

A finished dosage form of the plasmid DNA pCMV-VEGF165 should be suitable for intramuscular injections and should not significantly change properties of the active substance during long-term storage. A possible finished dosage form of the plasmid pCMV-VEGF165 includes, but is not limited to, a frozen solution, liquid solution, lyophilisate, i.e., a freeze-dried solution, and an amorphous film.

In one embodiment, a pharmaceutical composition comprises a preparation of purified plasmid DNA encoding a vascular endothelial growth factor (VEGF) under the control of functional genetic elements which provide gene expression in human cells, and an effective amount of at least one pharmaceutically acceptable excipient for providing an isotonic solution, wherein the at least one pharmaceutically acceptable excipient is at least one cryoprotectant which is a vehicle, a pH stabilizer or a combination thereof, wherein a concentration of the purified plasmid DNA is from 0.1 to 10 mg/ml, and a pH of the composition is form 7.0 to 9.0.

In another embodiment, the pharmaceutical composition comprises purified plasmid DNA and an effective amount of glucose and sodium phosphate for forming an isotonic solution for injections, wherein the pH of the composition is 7.8.

In yet, a different embodiment, the pH of the composition is from 7.2 to 8.5, and preferably from 7.4 to 8.2.

In one embodiment, the composition comprises purified plasmid DNA, from 200 to 400 mM of glucose and from 3 to 30 mM of sodium phosphate.

In a different embodiment, the pharmaceutical composition comprises from 0.8 to 1.2 mg/ml of the purified plasmid DNA pCMV-VEGF165, from 280 to 320 mM of dextrose; and from 8 to 12 mM of sodium phosphate, wherein the pH of the composition is from 7.4 to 8.2.

A more preferable variant of the finished dosage form is a liquid solution or a lyophilizate, as they can be stored at positive temperatures, i.e., in standard pharmaceutical refrigerators, and do not require a large period of time for preparing injections.

An even more preferable variant of the finished dosage form is a lyophilizate, as the lack of water potentially retards chemical reactions of DNA chain degradation which result in conversion of supercoiled plasmid DNA to the relaxed circular form. Moreover, when a liquid dosage form of plasmid DNA is stored, a long-term contact of the solution and a rubber seal material may occur, wherein the rubber seal may potentially contain extractable ions of transition metals which can accelerate degradation of DNA chains by way of catalyzing the formation of hydroxyl radicals.

The preparation of the lyophilizate, i.e., an amorphous or microcrystalline porous mass, requires the presence of excipients in a solution to be lyophilized which act as a cryoprotectant, pH stabilizer, chelating agent, antioxidant, and/or a vehicle. The minimum possible set of the excipients may include at least one cryoprotectant which has properties of a vehicle, a pH stabilizer, or a combination thereof. An excipient which is a cryoprotectant and a vehicle, may be at least one component selected from the group consisting of a mono- and disaccharide, polyol, and polymer, for example, selected from the group consisting of sucrose, lactose, trehalose, mannitol, sorbitol, glucose, raffinose, polyvinyl pyrrolidone, and a combination thereof. The pH stabilizer may be at least one component selected from the group consisting of sodium citrate, sodium phosphate, Tris-HCl, Tris-acetate, glycine, methionine, arginine, histidine, and other amino acids.

While studying various pharmaceutical compositions of the plasmid DNA pCMV-VEGF165, the inventor have surprisingly found that the greatest stability under storage conditions at a temperature of from +2 to +8° C. was provided by a combination of excipients such as glucose and sodium phosphate at a pH 7.8.

When the volume of a solution is the same before and after the lyophilization, the most optimal composition of the solution which provides preserved properties of the plasmid DNA pCMV-VEGF165 in the lyophilization process and further storage is as follows:

1. Concentration of the plasmid DNA is form 0.1 to 10 mg/ml, preferably from 0.5 to 4 mg/ml, and more preferably from 0.8 to 1.2 mg/ml.

2. Concentration of glucose (dextrose) is from 200 to 400 mM, preferably from 250 to 350 mM, and more preferably from 280 mM to 320 mM.

3. Concentration of sodium phosphate (a mixture of trisodium, disodium and monosodium phosphate) is form 3 to 30 mM, preferably from 5 to 20 mM, and more preferably from 8 to 12 mM.

4. The pH of the solution is from 7.0 to 9.0, preferably from 7.2 to 8.5, and more preferably from 7.4 to 8.2.

The structure of the plasmid used for preparation of a strain producer and a pharmaceutical composition are provided on FIG. 1.

Another object of the invention is a method for storage of purified plasmid DNA which encodes a vascular endothelial growth factor (VEGF) comprises adding a solution of at least one cryoprotectant to the purified plasmid DNA, thereby obtaining an isotonic solution, subsequently lyophilizing the isotonic solution, and storing the lyophilizate at a temperature of from +2° C. to +8° C., wherein a concentration of the purified plasmid DNA prior to the lyophilizing is from 0.1 to 10 mg/ml, and a pH of the isotonic solution is from 7.0 to 9.0.

In one embodiment, at least one cryoprotectant is glucose, and a mass ratio of glucose to the purified plasmid DNA in the isotonic solution is 1:50.

In a different embodiment, at least one cryoprotectant is glucose, and a proportion of relaxed plasmid DNA in the lyophilizate stored for 3 months is not more than 10%.

In yet another embodiment, at least one cryoprotectant is sodium phosphate, wherein a content of sodium phosphate is from 5 to 20 mM and the pH of the isotonic solution is from 7.8 to 9.0. Another object of the invention is a method for application of the pharmaceutical composition comprising applying an effective amount of the pharmaceutical composition for providing a therapeutic effect depending on a nosologic form and medical indication, to a human subject.

Having generally described an object of the invention, a further understanding can be obtained by reference to certain specific examples which are provided herein for purposes of illustration only, and are not intended to be limiting unless otherwise specified. It is appropriate to give examples on possible implementation of the invention: preparation of the plasmid DNA pCMV-VEGF165.

EXAMPLES

Example 1

Preparation of a Solution for the Purified Plasmid DNA pCMV-VEGF165

Preparation of Inoculums

A vial of preserved inoculums of the producer strain TOP10/pCMV-VEGF165 from the working bank was recovered from the working bank and the inoculum was cultured in 50 ml of a liquid medium.

Biosynthesis of pDNA

A fermenter with a 10-liter flask was prepared, the flask was sterilized with a medium, delivery and withdrawal lines were aseptically fix, a measuring set of connection parameters was calibrated, the fermenter was inoculated and cultured for 8 hours until a constant concentration of dissolved oxygen (stationary culture growth phase) was achieved with a fixed rate of a mixer of 1000 rot/min, after that aeration was stopped and the flask was cooled. A sample of a culture suspension was transferred for analysis of the culture density.

Production of Biomass

The biomass, i.e., the cell pellet, was separated from the culture liquid in an intermittent floor-standing high-rate centrifuge with a fixed-angle rotor. The supernatant of the cultural liquid was transferred to an autoclave for disinfection and neutralization. The derived biomass was kept in centrifuge bags at a low temperature in a refrigerator. A sample of the biomass was transferred for analysis of the content and integrity of the target substance.

Suspending Biomass, Lysis and Neutralization

Defrosted biomass was transferred to a lysis container and suspended with an overhead stirrer in a suspension solution. Cell lysis was performed with a solution of sodium hydroxide and sodium dodecyl sulfate by mixing with the overhead stirrer for 5 minutes. While mixing, a solution of potassium acetate was added for neutralization and simultaneous formation of the precipitate of cell debris, genomic DNA bound to histones and proteins. The precipitate was formed as a result of the transformation of sodium dodecyl sulfate into an insoluble potassium salt and micelle coagulation. At the same time, neutralization of the solution resulted in renaturation of the plasmid DNA.

Preparation of Clarified Lysine

The obtained suspension was transferred to centrifugation bags and the precipitate was separated in an intermittent floor-standing high-rate centrifuge with a fixed-angle rotor. The supernatant of the cultural liquid was transferred for disinfection and neutralization in an autoclave. The clarified solution of the plasmid DNA which also contained related compounds—a relaxed and linear form of the plasmid DNA, as well as foreign impurities such as residual genomic DNA, RNA, proteins and LAL-endotoxin was collected in the feed vessel of an ultrafiltration set.

Ultrafiltration

The solution of the plasmid DNA was concentrated by ultrafiltration in the tangential flow with hollow-fiber cartridges with the cutoff threshold of 500 kDa. As a part of the ultrafiltration, the additional 9-fold removal of the molecules having a size of less than 3 kDa also occurred, e.g., removal of proteins, transport RNA, LAL-endotoxin, and short fragments of genomic DNA. The solution was concentrated up to 9-folds. The concentrated plasmid solution was collected into a glass vial, the ultrafiltration unit was washed with a solution for gel filtration and combined with the concentrated solution of the plasmid DNA.

Gel Filtration

A first process of deep chromatographic purification by gel filtration on a coarse pored dextrin sorbent Sparse 6 Fast Flow "GE Life sciences" was performed. A solution having a high concentration of salt that contained 2.1 M of ammonium sulphate and 10 mM EDTA-Na was used that allowed to separate of molecules according to their size and to retain impurities of RNA and ALL-endotoxin with the sorbent due to the non-specific hydrophobic interaction. A solution with impurities and washing solutions were collected into a vessel and disposed in due course. A solution of half-purified plasmid DNA which contained 2.1 M of ammonium sulphate, was collected into a glass container.

Affine Chromatography

A second process of deep chromatographic purification by thiophilic (pseudoaffine) chromatography on a sorbent PlasmidSelect Xtra "GE Lifesciences" was conducted. To wash the column, a solution which contained 2.0 M of ammonium sulphate was used and a half-purified solution was applied to a column with the concentration of ammonium sulphate of 2.1 M. When the solution was applied, all DNA forms and the proportion of the residual DNA were adsorbed on the sorbent, wherein the residual proteins and endotoxin were not adsorbed.

After the application, the column was washed with an ammonium sulphate solution having the concentration of 2.0 M, wherein the residual DNA, genomic DNA and related compositions of the plasmid DNA are eluted. The active substance HSCI-01 was eluted with an ammonium sulphate solution having the concentration of 1.7 M. The column was regenerated and purified with a solution of sodium hydroxide having the concentration of 0.1 M. A solution of impurities and washing solutions was collected into a container and disposed in due course. A solution of half-purified plasmid DNA was collected which contained 1.7 M of ammonium sulphate into a glass container and diluted with water for injections at the ratio of 1:2.

Anion Exchange Chromatography

A third process of deep chromatographic purification by anion exchange chromatography on a sorbent SOURCE 30Q "GE Lifesciences" was conducted. An active substance was absorbed onto a column and rinsed with a solution containing 0.4 M of sodium chloride. When the column was washed, a cation of the active substance was substituted from ammonium ion to sodium ion, and residual endotoxin was eluted. The active substance was eluted with a solution of 1 M sodium chloride. A solution containing impurity and washing solutions was collected into a container and disposed in due course. A solution of the purified plasmid DNA was collected into a glass container.

Ultrafiltration and Diafiltration

The solution of the purified plasmid DNA was concentrated by ultrafiltration in a set with a hollow-fiber module with the cuttoff threshold of 300 kDa. When the concentration of 0.25% was achieved, the set was switched to the diafiltration mode and a complete buffer change with water for injections was performed. The filtrate was collected into a container and disposed in due course. The filtrate was poured into a glass container and the concentration of supercoiled plasmid DNA at a temperature below 70° C. was measured.

Example 2

Production of Lyophilizate Variants for Stability Studies

To derive variants of a pharmaceutical composition, a salt-free solution of the plasmid DNA pCMV-VEGF165 having the concentration of approximately 2.5 mg/ml and the residual content of Tris-HCl, pH=7.5, and NaCl not more 1 mM were used. As cryprotectants, glucose, sucrose and lactose were added which meet the requirements of not lower than that of the European Pharmacopeia. As a pH stabilizer, a solution of sodium phosphate having a pH from 7.2 to 9.0 was used. A saccharide at the final concentration of 300 mM and sodium phosphate at the final concentration of 10 mM were used. Such concentrations of the excipients provided isotonicity of the solution for endogenous administration. The final DNA concentration in the derived pharmaceutical compositions was 1 mg/ml.

The lyophilization was conducted in 5-ml glass vials which were equipped with half-opened lyophilization rubber seals and filled with 1.2 ml of test solutions. A regime of the lyophilization drying for all test samples is shown in Table 1 below.

TABLE 1

Regime of lyophilization drying.

| Stage | Duration, min. | Temperature, ° C. |
|---|---|---|
| 1) Solution freezing: | | |
| a) | 30 | −50 |
| b) | 300 | −50 |
| 2) Lyophilization: | | |
| a) | 60 | −30 |
| b) | 930 | −30 |
| c) | 60 | −10 |
| d) | 480 | −10 |
| e) | 60 | 20 |
| f) | 360 | 20 |
| 3) Final drying: | | |
| a) | 60 | 40 |
| b) | 600 | 40 |

The pressure in the working chamber in the drying process was 60 μbar, a product temperature upon completion of the freezing stage should not be greater than minus 45° C., i.e., 2 degrees C. lower than the glass transition temperature (Tg) of glucose and more than 10 degrees C. lower than Tg of all other sugars. A product temperature upon lyophilisation should be not lower than 15° C. A temperature of the products was measured with thermocouples frozen into the vials with product simulators which contain all excipients, except for DNA. Upon the final drying, the vials were pressurized in the atmosphere of sterile dried air with battery compression. The unloaded vials were closed with aluminum caps.

To compare stability of the product when stored at an elevated temperature, a solution of sodium phosphate having a pH 7.8 was used which was obtained by mixing disodium and monosodium phosphate solutions at the molar ratio of 91.5:8.5. The lyophilized closed vials were stored at +37° C. in a dry thermostat, wherein a set of vials was withdrawn once a month, the lyophilizate was dissolved and a proportion of the relaxed plasmid DNA was measured by analytic ion exchange chromatography. The results of the measurement are presented in Table 2.

TABLE 2

Proportion of relaxed plasmid DNA stored at an elevated temperature.

| | Retention time, months | | | |
|---|---|---|---|---|
| Cryoproprotectant | 0 | 1 | 2 | 3 |
| Glucose | 2.2% | 2.8% | 5.3% | 10.0% |
| Saccharide | 2.1% | 6.2% | 8.4% | 10.4% |
| Maltose | 2.3% | 7.0% | 8.8% | 14.6% |
| Lactose | 2.2% | 9.0% | 9.6% | 18.5% |

It was established that glucose which was used as a cryoprotectant provided the lowest degradation rate for supercoiled plasmid DNA at the mass ratio of the saccharide to DNA of 1:50 and a pH=7.8.

As for a pharmaceutical composition containing glucose, the relationship between stability of the supercoiled plasmid DNA and the pH of the solution and the concentration of sodium phosphate (pH 7.8) was investigated. It was established that stability of the supercoiled plasmid DNA had not significantly changed for various concentrations of sodium phosphate from 5 to 20 mM (data are not shown). For various pH of the solution, it was shown (see Table 3) that there were no significant changes in stability for the pH range from 7.8 to 9.0, but stability of the supercoiled plasmid DNA was decreased for the pH 7.2.

TABLE 3

Proportion of relaxed plasmid DNA stored at an elevated temperature and various pH levels.

| pH | 0 mon. | 1 mon. | 2 mon. | 3 mon |
|---|---|---|---|---|
| 7.2 | 2.2% | 4.09% | 7.63% | 15.17% |
| 7.8 | 2.2% | 2.80% | 5.30% | 10.00% |
| 8.4 | 2.3% | 2.76% | 3.34% | 10.69% |
| 9 | 2.1% | 2.51% | 2.97% | 8.39% |

Thus, in accordance with the accelerated storage data, a pharmaceutical composition may be selected when a pH range of the composition is from 7.8 to 9.0 and the concentration of sodium phosphate is from 5 to 20 mM. As the concentration of ionized phosphate groups in DNA with a DNA concentration of 1 mg/ml is approximately 3 mM, and a concentration of buffer salts should significantly exceed the total concentration of ionized groups in an active substance, the optimal concentration of sodium phosphate was selected to be 10 mM. The optimal pH of the solution was 7.8, as such value is the closest to the physiological pH (7.2-7.4). However, it should be considered that the pH should be as close to 7.2 as possible, and the higher pH level, the higher plasmid stability (up to 9.0). Probably, plasmid DNA preserves its stability at a storage temperature from +2 to +8° C. and a pH 7.0-9.0, which is sufficient for gene therapy.

Example 3

Formulation of a Solution of Purified Plasmid DNA and Production of the Finished Dosage Form The plasmid DNA, as shown in Example 1, was obtained prior to the end of the stage of anion exchange chromatography. The following stages were performed as described below.

Ultrafiltration and Diafiltration

A solution of the purified plasmid DNA was concentrated by ultrafiltration in a set with a hollow-fiber module with the cuttoff threshold of the membrane 300 kDa. When the concentration of 0.15% was achieved, the set was switched to the diafiltration mode and the complete buffer change was performed for a solution of sodium phosphate having concentration of 10 mM and a pH 7.8 containing 4.4% (300 mM) of glucose in water for injections. The filtrate was collected into a container and was disposed in due course. The concentrated formulated solution was poured into a glass container, the concentration of the supercoiled plasmid DNA was measured and the solution was brought up to the final DNA concentration of 0.1%.

Sterile Filtration

The finished substance solution was transferred into a clean area of class A and sterile filtration with a disk membrane filter in depyrogenized sterile 250-ml containers for infusion solutions per GOST 19808-86 was conducted. Samples to be transferred to the quality control department were selected, the containers were closed with rubber seals, then closed with aluminum caps and were frozen in a quarantine zone of a warehouse.

The formulated solution of a plasmid DNA solution was defrosted and transferred to a clean area of class A. The containers were opened and sterile filtration was performed with disk membrane filters to depyrogenized sterile 250-ml containers for infusion solutions according to GOST 19808-86. The solution was poured at sterile conditions into sterile 5-ml insulin vials according to GOST 19808-86. The vials were closed with rubber seals according to TU 38.006.269-90 and transferred for freeze drying.

The vials were places on the racks of a freeze dryer, were frozen at −45° C. and a 3-stage vacuum drying was performed. Seals were placed, the vials were withdrawn and were closed with aluminum caps according to GOST P 51314-99.

Example 4

Verification of Stability of the Finished Dosage Form of pCMV-VEGF165

Vials with the sterile lyophilizate of the plasmid DNA pCMV-VEGF165 were stored in a pharmaceutical refrigerator at +4° C. for 2.5 years and the analysis of the proportion of related impurities was conducted by ion exchange chromatography once in 6 months. The results of the analysis are presented in Table 4.

TABLE 4

Stability of finished dosage form kept in temperature +4° C.

| Standard | At release | 6 months | 12 months | 18 months | 24 months | 30 months |
|---|---|---|---|---|---|---|
| Relaxed and linear plasmid DNA less than 5%, according to ion exchange HPLC | 3.0% | 3.0% | 3.3% | 3.7% | 4.1% | 4.0% |

Thus, the dosage form of the plasmid DNA pCMV-VEGF165 was stable for at least two years.

Example 5

Verification of Efficiency of the Pharmaceutical Composition

The efficacy of treatment with a pharmaceutical composition which contains excipients, in addition to the plasmid construction, was confirmed in patients with chronic lower limb ischemia, i.e., the results of treatment with the pharmaceutical composition containing the excipients were unexpectedly superior compared to treatment with a composition including only the plasmid (monotherapy). The higher treatment efficacy was determined in the study which involved 75 patients with chronic lower limb ischemia (2a-3 stage according to A. V. Pokrovsky-Fontaine (A. V. Pokrovsky, 2004; Inter-Society Consensus for the Management of Peripheral Arterial Disease (TASC II). Eur. J. Vasc. Endovasc. Surg., oxygen pressure, ankle-brachial index and a linear blood flow rate in the posterior tibial artery.

Walking Distance.

After 3 months of treatment, a walking distance in patients of the clinical group was 236.49±193.49 m (average distance), and in 6 months −284.73±242.02 m (average distance) (from 20 to 1500 m of all obtained distances). The increase of the mean distance which a patient could walk without pain was 149.47 m in the study group, wherein the median had increased by 127.5 m and the difference between the values was statistically significant (p=0.006).

In the control group, the mean distance which a patient could walk without pain decreased by 1.42 m, the median had increased by 35.00 m, and the difference between the values were not statistically significant (p=0.6). The differences in value dynamics between the groups (+150.89 for the mean value and +92.5 for the median) were statistically significant (p=0.001).

Transcutaneous Pressure of Oxygen.

In the clinical group, there was a tendency for a stable increase of the mean value of TPO from 76.69±9.96 mm Hg at the first visit to 85.42±10.87 mm Hg at the fourth visit. The control group had opposite dynamics, i.e., there was a decrease of the mean value from 76.89±55.76 mm Hg to 75.37±61.57 mm Hg for the same observation period. The observed differences between the values in the clinical group were significant, and the difference in the control group were not significant (p=0.096), i.e., the values of the patients almost had not changed as a part of standard treatment. The recorded differences in the increased mean TPO values between the groups (+10.25) and the median (+8.00) were statistically significant (p=0.0001). The relative increase of the values in the groups was: +12.40±17.69% in the clinical group and 2.12±4.38% in the control group (p=0.001).

Ankle-Brachial Index.

The ABI of the target lower extremity had a tendency to increase in the patients of the clinical group and to decrease in the patients of the control group. Thus, in the clinical group, the baseline value 0.513±0.182 had increased during therapy by 0.057 and was 0.57 at six months. The observed difference of the values between fourth and first visits in the clinical group was significant (p=0.001). In the control group, the index had decreased by 0.02 units in six months, i.e., from 0.458±0.182 to 0.438±0.187. However, the changes were not significant (p=0.5).

The difference between the increased mean ABI values between the groups was +0.077 (median +0.065), the recorded differences were significant.

Linear Blood Flow Rate (According to Ultrasound Doppler Sonography of the Posterior Tibial Artery).

In the patients of the clinical group, the value had a tendency to increase during the study period: the mean value had increased by 8.24 cm/sec, the median—by 5.0 cm/sec, i.e., from 14.95±10.19 cm/sec up to 23.19±12.71 cm/sec in 6 months.

In the patients of the control group, the value had increased by 1.30 cm/sec (from 17.60±6.60 cm/sec at the beginning of the study, up to 18.90±6.77 cm/sec at six months), while the median had not changed, i.e., was at the level of 20.0 cm/sec. During the study, the differences between the groups were statistically significant (p=0.005).

The mean values in the clinical group had increased to a greater extent compared to the values shown by the control group (+6.94 cm/sec), as well as the median (+5.00 cm/sec); the difference in the values was statistically significant (p=0.005).

Thus, based on the efficiency criterion of the "walking distance without pain," the values had significantly increased in patients from 135.3 m at the first visit to 248.7 m at six months (the increase of 110.5%) which is significantly different from the trend in the control group (p=0.001).

Additional Efficiency Criteria:

ABI—increased by 11.11% (p=0.001);

TPO—increased by 11.38% (p=0.001);

LBFR—increased by 55.12% (p=0.001).

RU patent application RU2012137126, filed Aug. 31, 21012, is incorporated herein by reference.

Numerous modification and variations on this invention are possible in light of the above teachings. It is therefore to be understood that within the scope of the appended claims, this invention may be practiced otherwise than as specifically described herein.

The invention claimed is:

1. A pharmaceutical composition for induction of blood vessel tissue growth, the composition comprising:

purified plasmid DNA encoding a human recombinant vascular endothelial growth factor (VEGF), wherein the VEGF encoding sequences are operatively linked to expression control sequences to provide gene expression in human cells, and from 200 to 400 mM of glucose and from 3 to 30 mM of sodium phosphate, wherein the pharmaceutical composition is an isotonic solution, and wherein a concentration of the purified plasmid DNA in the composition is from 0.1 to 10 mg/ml, and a pH of the composition is form 7.0 to 9.0.

2. The pharmaceutical composition according to claim 1, wherein the pH of the composition is from 7.8 to 9.0.

3. The pharmaceutical composition according to claim 2, comprising from 5 to 20 mM of the sodium phosphate.

4. The pharmaceutical composition according to claim 1, wherein the pH of the composition is from 7.4 to 8.5.

5. The pharmaceutical composition according to claim 1, wherein the pH of the composition is from 7.4 to 8.2.

6. The pharmaceutical composition according to claim 1, wherein the concentration of the purified plasmid DNA in the composition is from 0.5 to 4 mg/ml.

7. The pharmaceutical composition according to claim 1, wherein the concentration of the purified plasmid DNA in the composition is from 0.8 to 1.2 mg/ml.

8. The pharmaceutical composition according to claim 1, wherein the purified plasmid DNA is pCMV-VEGF165.

9. The pharmaceutical composition according to claim 1, wherein the purified plasmid DNA comprises the polynucleotide sequence of SEQ ID NO:1.

10. The pharmaceutical composition according to claim 1, wherein not less than 70% of the purified plasmid DNA is present in a supercoiled form.

11. The pharmaceutical composition according to claim 1, wherein the the purified plasmid DNA comprises not more than 5% of impurities selected from the group consisting of a relaxed ring form, a linear plasmid form, and a mixture thereof, not more than 1% of genomic DNA, not more than 1% of RNA, not more than 0.1% of total protein, and not more than 50 EU of an endotoxin per 1 mg of an active substance.

12. A pharmaceutical composition for induction of blood vessel tissue growth the composition comprising from 0.8 to 1.2 mg/ml of the purified plasmid DNA comprising the polynucleotide sequence of SEQ ID NO: 1;

from 280 to 320 mM of dextrose; and from 8 to 12 mM of sodium phosphate, wherein the pH of the composition is from 7.4 to 8.2.

13. A method for storage of purified plasmid DNA which encodes a human recombinant vascular endothelial growth factor (VEGF), the method comprising:

adding from 200 to 400 mM of glucose and from 3 to 30 mM of sodium phosphate to the purified plasmid DNA, thereby obtaining an isotonic solution, subsequently lyophilizing the isotonic solution, thereby obtaining a lyophilizate, and storing the lyophilizate at a temperature of from +2° C. to +8° C., wherein a concentration of the purified plasmid DNA in the isotonic solution prior to the lyophilizing is from 0.1 to 10 mg/ml, and a pH of the isotonic solution is from 7.0 to 9.0.

14. The method according to claim 13, wherein a mass ratio of glucose to the purified plasmid DNA in the isotonic solution is 1:50.

15. The method according to claim 14, wherein a proportion of relaxed plasmid DNA in the lyophilizate stored for 3 months is not more than 10%.

16. The method according to claim 14, wherein the at comprising from 5 to 20 mM of the sodium phosphate and the pH of the isotonic solution is from 7.8 to 9.0.

17. The method of claim 13, wherein the purified plasmid DNA comprises the polynucleotide sequence of SEQ ID NO:1.

18. A pharmaceutical composition comprising:

purified plasmid DNA encoding a human recombinant vascular endothelial growth factor (VEGF), wherein the VEGF encoding sequences are operatively linked to expression control sequences to provide gene expression in human cells, and wherein the purified plasmid DNA comprises the polynucleotide sequence of SEQ ID NO:1, and from 3 to 30 mM of sodium phosphate and from 200 to 400 mM of glucose to make the pharmaceutical composition isotonic, and wherein a concentration of the purified plasmid DNA in the composition is from 0.1 to 10 mg/ml, and a pH of the composition is form 7.4 to 9.0.

19. The method of claim 18, wherein the pH of the composition is from 7.8 to 9.0.

* * * * *